US011571118B2

(12) United States Patent
Norton et al.

(10) Patent No.: US 11,571,118 B2
(45) Date of Patent: Feb. 7, 2023

(54) DEVICES AND SYSTEMS FOR USE IN LAPAROSCOPIC SURGERY

(71) Applicant: Axcess Instruments Inc., Tyler, TX (US)

(72) Inventors: Michael J. Norton, Tyler, TX (US); Noel D. Ischy, Tyler, TX (US)

(73) Assignee: Axcess Instruments Inc., Tyler, TX (US)

( * ) Notice: Subject to any disclaimer, the term of this patent is extended or adjusted under 35 U.S.C. 154(b) by 0 days.

(21) Appl. No.: 17/188,945

(22) Filed: Mar. 1, 2021

(65) Prior Publication Data

US 2021/0259537 A1  Aug. 26, 2021

Related U.S. Application Data

(60) Provisional application No. 62/983,026, filed on Feb. 28, 2020.

(51) Int. Cl.
| | |
|---|---|
| *A61B 1/313* | (2006.01) |
| *A61B 1/00* | (2006.01) |
| *A61B 1/045* | (2006.01) |
| *A61B 1/06* | (2006.01) |
| *A61B 1/018* | (2006.01) |
| *A61M 13/00* | (2006.01) |
| *A61B 1/12* | (2006.01) |
| *A61B 1/32* | (2006.01) |
| *A61B 17/34* | (2006.01) |
| *A61B 90/30* | (2016.01) |

(52) U.S. Cl.
CPC ........ *A61B 1/3132* (2013.01); *A61B 1/00006* (2013.01); *A61B 1/00045* (2013.01); *A61B 1/00137* (2013.01); *A61B 1/018* (2013.01); *A61B 1/045* (2013.01); *A61B 1/0684* (2013.01); *A61B 1/126* (2013.01); *A61B 1/32* (2013.01); *A61B 17/3423* (2013.01); *A61M 13/003* (2013.01); *A61B 90/30* (2016.02); *A61B 2017/3433* (2013.01); *A61B 2017/3484* (2013.01)

(58) Field of Classification Search
CPC ..... A61B 17/02; A61B 17/34; A61B 17/0218; A61B 17/3423; A61B 1/32; A61B 1/3132; A61B 1/045; A61B 1/00045; A61B 1/068; A61B 1/00; A61B 1/313; A61B 90/30; A61B 90/361; A61M 13/00; A61M 13/003
See application file for complete search history.

(56) References Cited

U.S. PATENT DOCUMENTS 10,278,730 B2 * 5/2019 Norton ................... A61B 90/30
2007/0265566 A1 * 11/2007 Simpson ............. A61M 5/3216
604/110

* cited by examiner

*Primary Examiner* — Vi X Nguyen
(74) *Attorney, Agent, or Firm* — Locke Lord LLP; Scott D. Wofsy; Daniel J. Fiorello

(57) ABSTRACT

An access device for a minimally invasive procedure can include a port body defining an instrument channel for a medical instrument, a radial extension extending at least partially outward from the body in a radial direction. The radial extension can extend from a distal end of the port body. The radial extension can define an imaging device cavity defined therein spaced from the port body and opening distally from the radial extension. The imaging device cavity can be configured to receive an imaging device therein for providing images within a field of view that is at least partially distal of the port body.

12 Claims, 12 Drawing Sheets

DEVICES AND SYSTEMS FOR USE IN LAPAROSCOPIC SURGERY

CROSS-REFERENCE TO RELATED APPLICATIONS

This application claims priority to and the benefit of U.S. Provisional Application No. 62/983,026, filed Feb. 28, 2020, the entire contents of which are herein incorporated by reference in their entirety.

FIELD

This disclosure relates to surgery, and more particularly, to devices and systems for use in laparoscopic medical procedures.

BACKGROUND

Laparoscopic surgery is widely practiced in multiple specialties of medicine. In most situations it requires the insertion of a cannula and a laparoscope. Additional cannulas or other surgical instruments can be placed while under vision through a laparoscope. This requires an organized operational space to function together or independently. Laparoscopes for performing these procedures have been used in various forms for nearly 100 years. They are significant in size and require an accompaniment of support equipment for effective imaging of the operative site. It would be useful therefore, to reduce the size and format of this physical imaging instrument while increasing its visual, lighting and format capabilities. This would further enable ancillary surgical instruments.

Such conventional methods and systems have generally been considered satisfactory for their intended purpose. However, there is still a need in the art for improved medical devices. The present disclosure provides a solution for this need.

SUMMARY

In accordance with at least one aspect of this disclosure, an access device for a minimally invasive procedure can include a port body defining an instrument channel for a medical instrument and at least one radial extension extending at least partially outward from the body in a radial direction. The radial extension can extend from a distal end of the port body. The radial extension can include an imaging device cavity defined therein radially spaced from the port body and opening from the radial extension. The imaging device cavity can be configured to receive an imaging device therein for providing images within a field of view that is at least partially distal of the port body.

In certain embodiments, the port body and the radial extension can be integrally formed. The port body and/or the radial extension can define one or more lighting channels therethrough from a proximal side of the port body to the distal side of the port body and/or the radial extension. The one or more lighting channels can include two lighting channels spaced from each other in a transverse direction that is perpendicular relative to the radial direction. The one or more lighting channels can be positioned radially between the imaging device cavity and the instrument channel.

In certain embodiments, the device can include an imaging cable channel defined in the port body and the radial extension between a proximal side of the port body and the imaging device cavity to allow an imaging cable to pass therethrough from the imaging device to an imaging circuit board. An insufflation channel can be defined through the port body on an opposite side of port body from radial extension. Any other suitable location for any suitable internal channels are contemplated herein.

In certain embodiments, the radial extension can include a lip extending distally from a radially outward portion of the radial extension. The lip can be outward of the imaging device cavity for example.

In certain embodiments, the device can include one or more irrigation channels defined through port body and the radial extension such that one or more first irrigation openings (e.g., inlets) are defined in the port body and one or more second irrigation openings (e.g., outlets) are defined in the lip. The one or more irrigation channels can at least partially travel around the instrument channel, travel outwardly, then curve back inwardly within the radial extension to the one or more irrigation outlets defined in the lip.

The port body and the radial extension can form a boot shape. The radial extension can be a boot tip of the boot shape, for example. In certain embodiments, the radial extension extends from the port body a distance that is about equivalent to a widest part of the port body or less. The imaging device cavity can be positioned about halfway or more along a radial length of the radial extension. The instrument channel and the imaging device cavity can be configured such that an instrument channel centerline and an imaging device field of view centerline can intersect.

In certain embodiments, the device can further include an instrument seal disposed at distal opening of the instrument channel, an imaging device disposed within the imaging device cavity and having a cable extending through cable channel, and a transparent cover fixed to a distal side of the device and covering the imaging device, the transparent cover including a hole defined complimentary to the instrument channel and/or configured to retain the instrument seal in the instrument channel. The device can include an auxiliary module configured to attach to a proximal side of the port body and connect to the imaging device. Any other suitable components (e.g., one or more lights, one or more light or imaging controllers, one or more circuit boards, one or more displays) are contemplated herein.

In accordance with at least one aspect of this disclosure, an imaging system for laparoscopic surgery can include an access device having an elongated body defining at least one access port and including a radial extension at a distal end thereof, a lighting device operatively associated with the radial extension of the access device, and at least one imaging device operatively associated with the radial extension of the access device.

The system can include a lighting control module for controlling the lighting device. The system can include a video control module for controlling the at least one imaging device. In certain embodiments, the system can include an image steering device operatively associated with the at least one imaging device. The system can include at least one image display device for displaying video acquired by the at least one imaging device.

In accordance, an imaging device for a minimally invasive procedure can include a body (e.g., without an instrument channel), at least one radial extension extending at least partially outward from the body in a radial direction. The radial extension can extend from a distal end of the body. The radial extension can include an imaging device cavity defined therein spaced (e.g., radially) from the port body and opening from the radial extension. The imaging device cavity can be configured to receive an imaging device therein for providing images within a field of view that is at least partially distal of the body.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
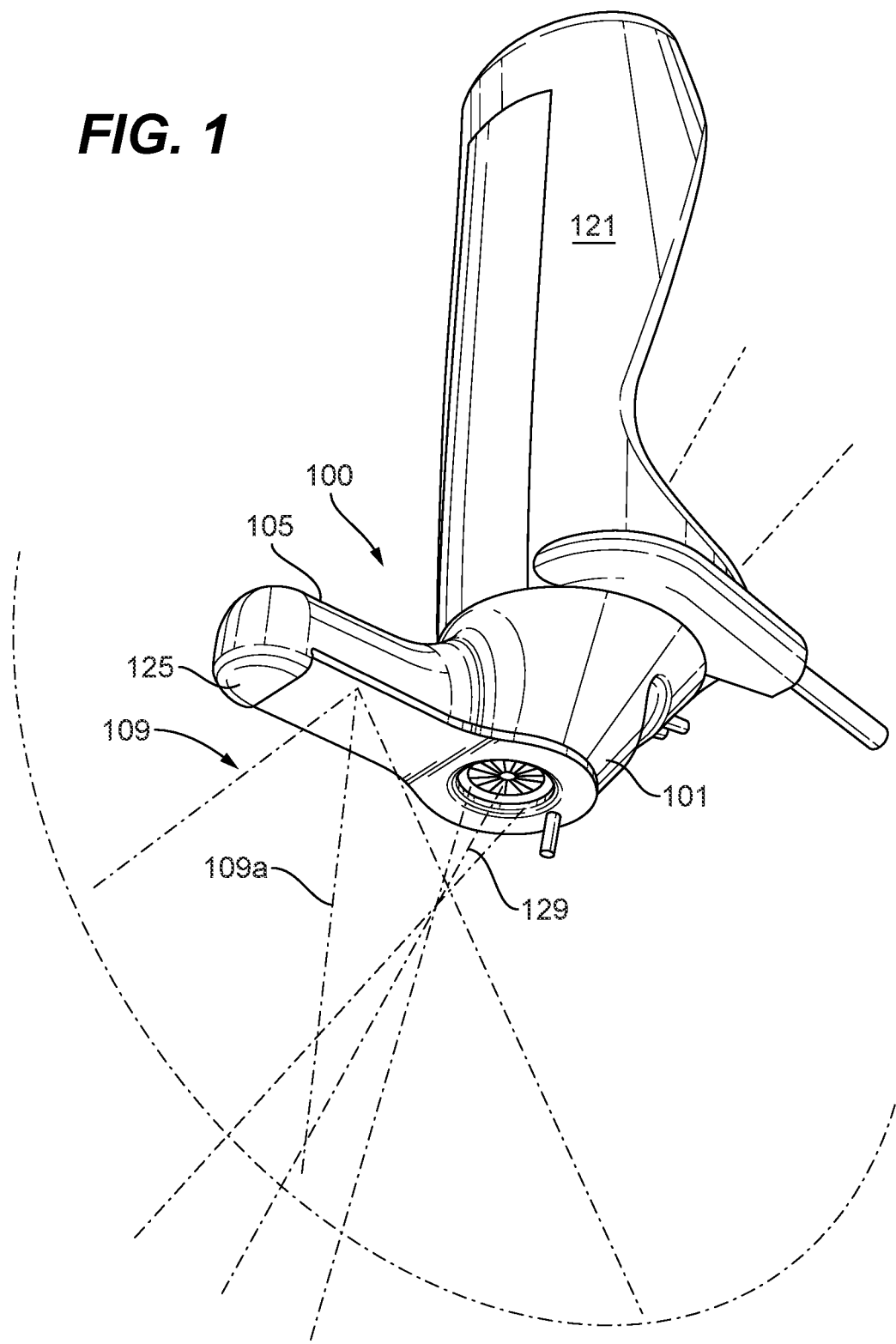
FIG. 1 is a perspective view of an embodiment of a device in accordance with this disclosure.

Reference will now be made to the drawings wherein like reference numerals identify similar structural features or aspects of the subject disclosure. For purposes of explanation and illustration, and not limitation, an illustrative view of an embodiment of a device in accordance with the disclosure is shown in FIG. 1 and is designated generally by reference character 100. Other embodiments and/or aspects of this disclosure are shown in FIGS. 2-11.

In accordance with at least one aspect of this disclosure, referring to FIGS. 1-4, an access device 100 for a minimally invasive procedure can include a port body 101 defining an instrument channel 103 (e.g., an instrument channel) for a medical instrument. The device can include a radial extension 105 extending at least partially radially outward from the body 101 in a radial direction (e.g., radial relative to the instrument channel 103 and/or an axis thereof).

Figure 2:
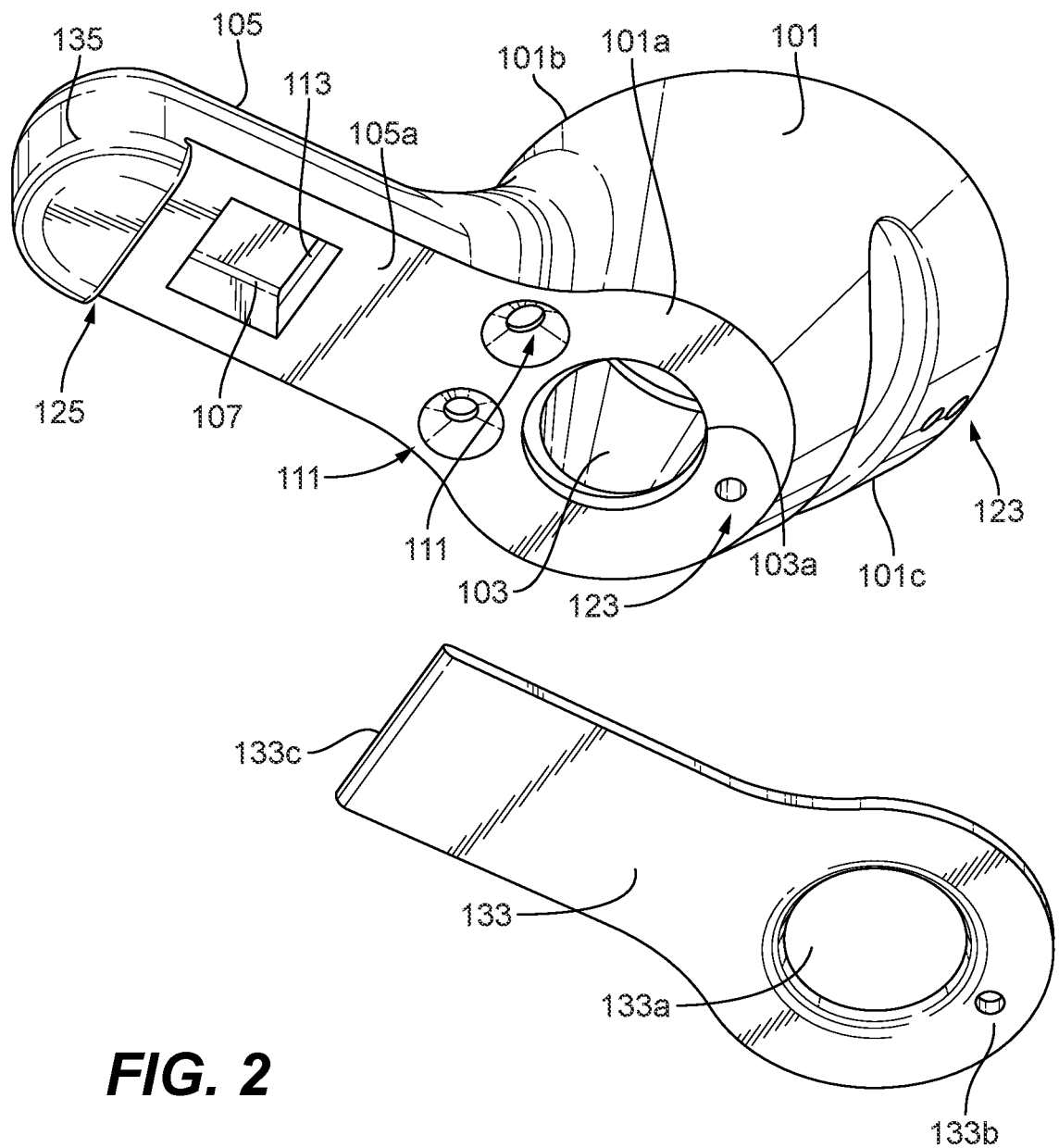
FIG. 2 is a perspective, exploded view of a portion of the device of FIG. 1, showing an access device and a transparent lower surface thereof.
Figure 3:
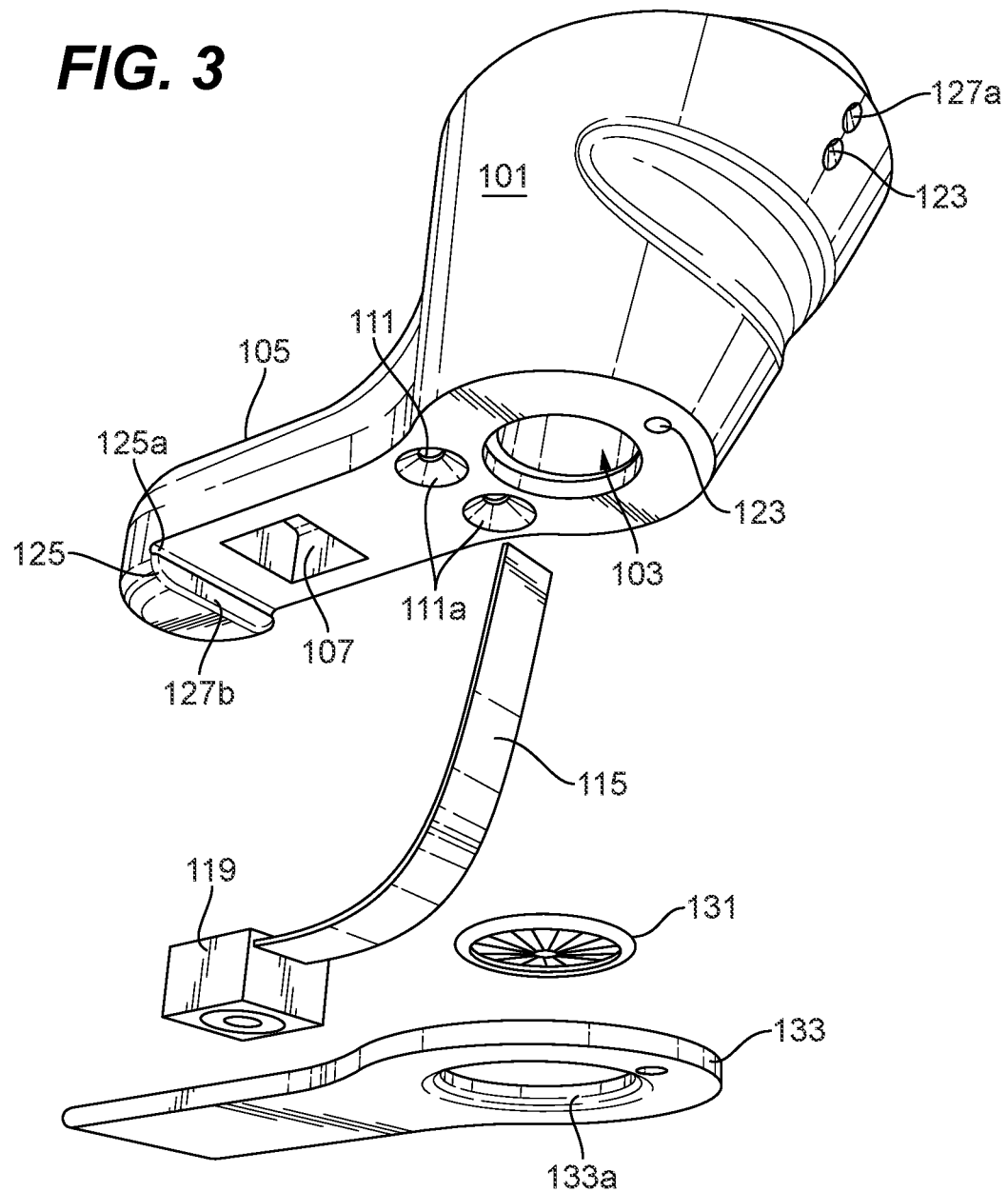
FIG. 3 is a perspective, exploded view of a portion of the device of FIG. 1, showing additionally an imaging device and an instrument seal.

The radial extension 105 can extend from a distal end 101a of the port body 101. As shown in FIGS. 2 and 3, the radial extension 105 can define an imaging device cavity 107 defined therein radially spaced from the port body 101 and opening distally from the radial extension 105. The imaging device cavity 107 can be configured to receive an imaging device (e.g., a camera) therein for providing images within a field of view 109 that is at least partially distal of the port body 101.

In certain embodiments, the port body 101 and the radial extension 105 can be integrally formed, e.g., as shown. In certain embodiments, any other suitable arrangement is contemplated herein. The distal opening 103a can be centered on a distal surface 101a of the port body 101. A proximal opening 103b can be similarly positioned. However either opening 103a, 103b may be in any other suitable position and have any other suitable shape as desired for performing any suitable surgical task, for example. As shown, the instrument channel 103 can include a reducing shape between the proximal opening 103b and the distal opening 103a. Any other suitable shape for the instrument channel 103 is contemplated herein.

The port body 101 can include a concave surface 101c that can facilitate stabilizing the device to an abdominal wall or fascia. Any other suitable external features and/or shapes for the port body 101 are contemplated herein (e.g., an auxiliary module attachment lip 101d extending from proximal opening.

Figure 11:
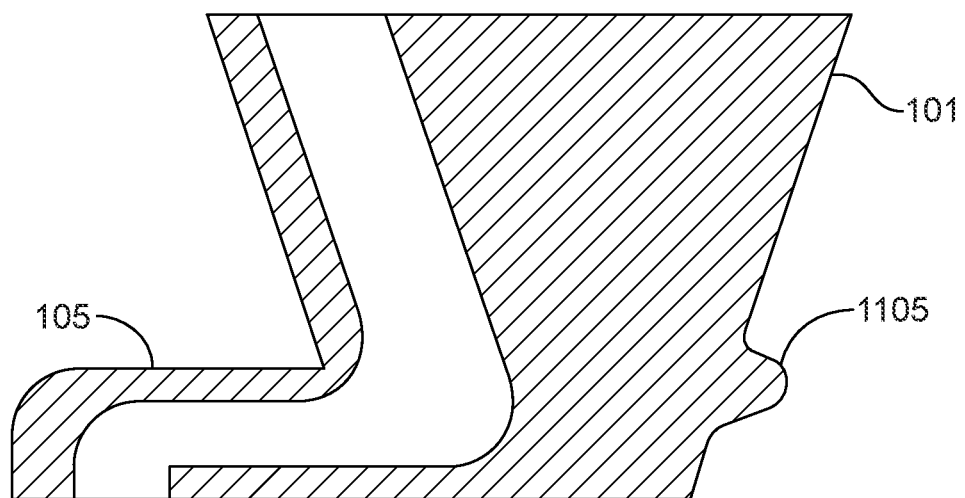
FIG. 11 is a cross-sectional schematic view of an embodiment of a device in accordance with this disclosure, wherein the device may include a second radial extension and/or not include an instrument channel to be used for imaging only.

For example, as shown in FIG. 11, in certain embodiments, the device 1100 can include a second radial extension 1105 extending from the lower half (or any other suitable location) of the port body 101 (e.g., in an opposite direction of the radial extension 105). The second radial extension 1105 can act as an anchoring point to stabilize the position of the device. In certain embodiments, the device 1100 does not include an instrument channel, e.g., as shown in FIG. 1, such that the device 1100 can be used for imaging only (e.g., to replace a laparoscope). The device 1100 can include any suitable structure (e.g., channels, cavities, etc.) as disclosed herein. For example, the device 1100 can be the same or similar to any embodiment of the device 100 disclosed herein except that device 1100 does not include an instrument channel 103. Any other suitable features are contemplated herein for device 1100.

The port body 101 and/or the radial extension 105 can define one or more lighting channels 111 therethrough from a proximal side 101b of the port body 101 to the distal side 101a of the port body 101 and/or the distal side 105a of the radial extension 105. In certain embodiments, the radial extension distal side 105a and the port body distal side 101a can form a continuous flat surface, e.g., as shown. Any other suitable arrangement is contemplated herein.

As shown, the one or more lighting channels 111 can include two lighting channels 111 spaced from each other in a transverse direction that is perpendicular relative to the radial direction, for example, e.g., circumferentially around the instrument channel 103 (e.g., the light channels 111 opening to the distal opening 103a thereof). The one or more lighting channels 111 can be positioned radially between the imaging device cavity 107 and the instrument channel 103, for example. Any suitable number of lighting channels 111 in any suitable position (e.g., a perimeter of lighting channels about the distal side 101a of the port body 101 and or the distal side 105a of the radial extension 105) are contemplated herein.

Figure 4:
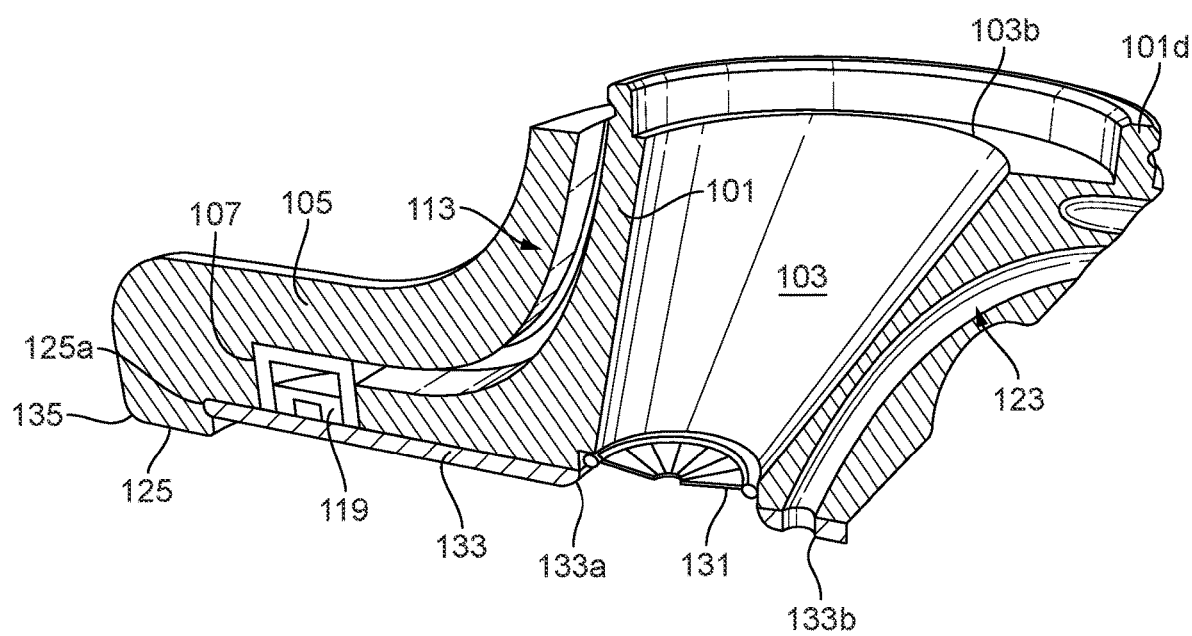
FIG. 4 is a cross-sectional view of the portion of the device as shown in FIG. 3.

As shown best in FIG. 4, the one or more lighting channels 111 can include a pot 111a at the distal end thereof. The pot 111a can disperse light, or be an area for a lighting element (e.g., an LED) to sit. In certain embodiments, the one or more lighting channels 111 can be configured to hold an optical fiber, optical medium, or otherwise be configured to transmit light from a source proximal of the distal side 101a, 105a (e.g., the fibers being fixed or steerable in any suitable manner to control lighting direction). For example, in certain embodiments, one or more light elements (e.g., LEDs) or optical connectors for connecting to external light elements, can be disposed in a proximal side 101b of the port body 101 and controllable or accessible to allow light to pass through one or more light channels 111.

In certain embodiments, a light element can be disposed at the distal side 101a, 105a (e.g., in the pots 111a) and wires can pass through the one or more lighting channels 111 to a power source, controller, or other mechanisms (e.g., for steering). Any other suitable lighting arrangement is contemplated herein. Lighting channels 111 and/or pots 111a can be the installation site for lighting mechanicals which may include LED lights, light pipes, power connections, light reflectors, and/or heat sink materials, and/or any other suitable lighting components.

Referring additionally to FIGS. 5-7B, in certain embodiments, the device 100 can include an imaging cable channel 113 defined in the port body 101 and the radial extension 105 between a proximal side 101b of the port body 101 and the imaging device cavity 107 to allow an imaging cable 115 (operatively connected to an imaging device 119) to pass therethrough to an imaging circuit board 117 (e.g., disposed within an auxiliary module 121). The imaging device cavity 107 can be configured to house a camera and lens and can be used to mount, contain, secure, and protect the imaging device 119. The imaging device cavity can also be the exit site for the chase that contains the communication cable such as a MIPI cable, power cable, warming device, measuring instruments, and/or associated communication cables. In certain embodiments, the circuit board 117 (e.g., or as shown FIG. 7B) and/or any other suitable components can be housed within the radial extension 105 and/or the port body 101, and can be wired and/or wireless.

In certain embodiments, an insufflation channel 123 can be defined through the port body 101 on an opposite side of port body 101 from the radial extension 105 (e.g., with an outlet on the distal side 101a of the port body 101). Any other suitable position for the insufflation channel 123 is contemplated herein. Any other suitable location for any suitable internal channels are contemplated herein.

In certain embodiments, the radial extension 105 can include a lip 125 extending distally from a radially outward portion of the radial extension 105. The lip 125 can be radially outward of the imaging device cavity 107 for example. As shown the lip 125 can include a convex surface 135 radially oriented to the body of the device 100 at the lip 125 for providing a smooth radial end. Any suitable smooth edge (e.g., a bevel, a curve) is contemplated herein.

Figure 5:
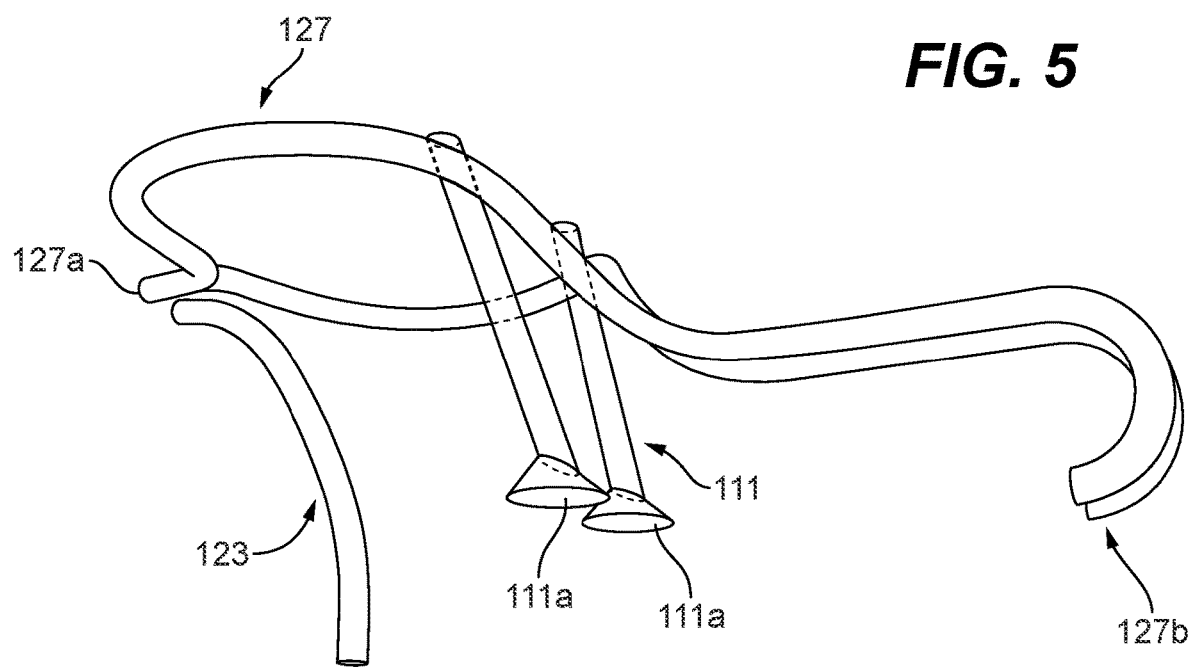
FIG. 5 is a perspective schematic view showing an embodiment of internal channels of the portion of the device shown in FIGS. 2 and 3.

In certain embodiments, the device 100 can include one or more irrigation channels 127 defined through port body 101 and the radial extension 105 such that one or more first irrigation openings 127a (e.g., inlets) are defined in the port body 101 and one or more second irrigation openings 127b (e.g., outlets) are defined in the lip 125. As shown in FIG. 5, the one or more irrigation channels 127 can at least partially travel around the instrument channel 103, travel radially outwardly (e.g., toward the end of the radial extension 105), then curve back radially inwardly (e.g., a U-turn as shown) within the radial extension 105 to the one or more irrigation openings 127b defined in the lip 125.

Figure 6:
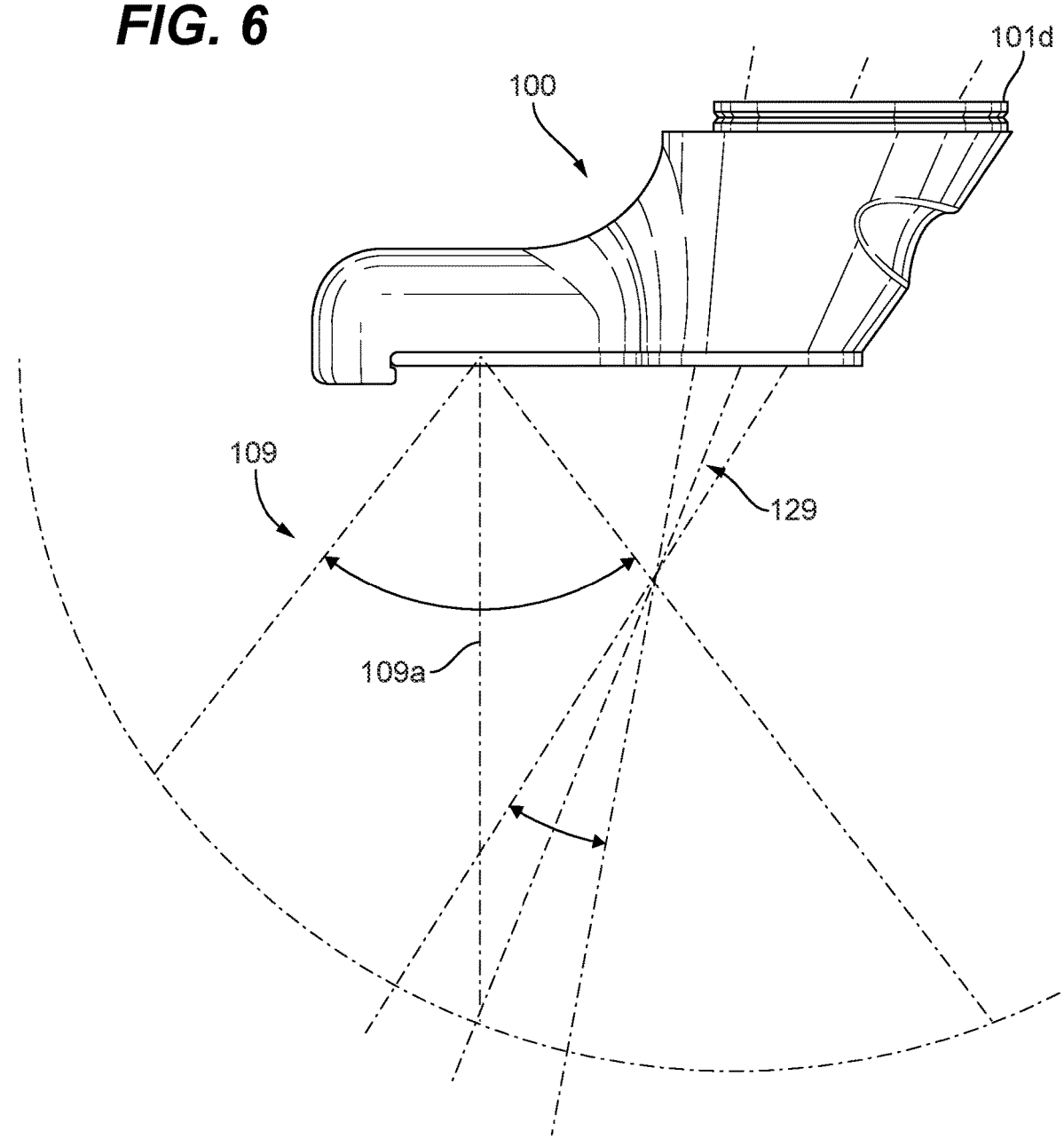
FIG. 6 is a side view of the portion of the device of FIG. 3, showing a relationship between the field of view and a centerline of an instrument channel of the access port.
Figure 7A:
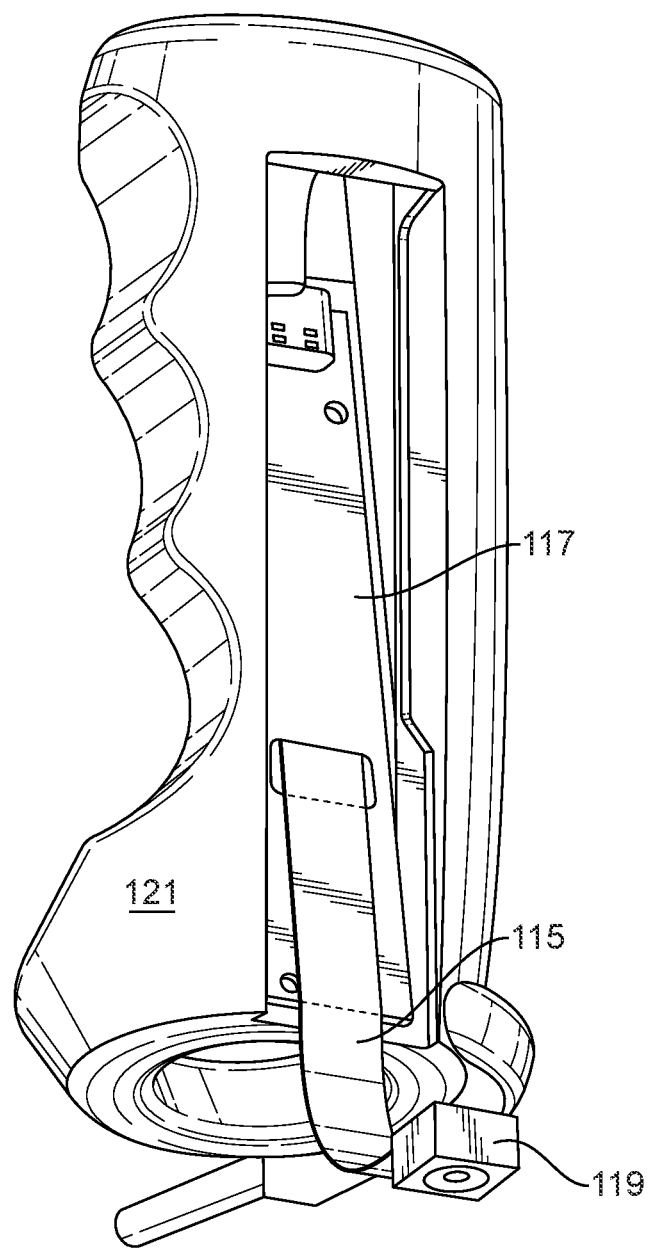
FIG. 7A is a perspective view of an embodiment of an auxiliary module of the embodiment of FIG. 1, showing an imaging circuit disposed in the auxiliary module.
Figure 7B:
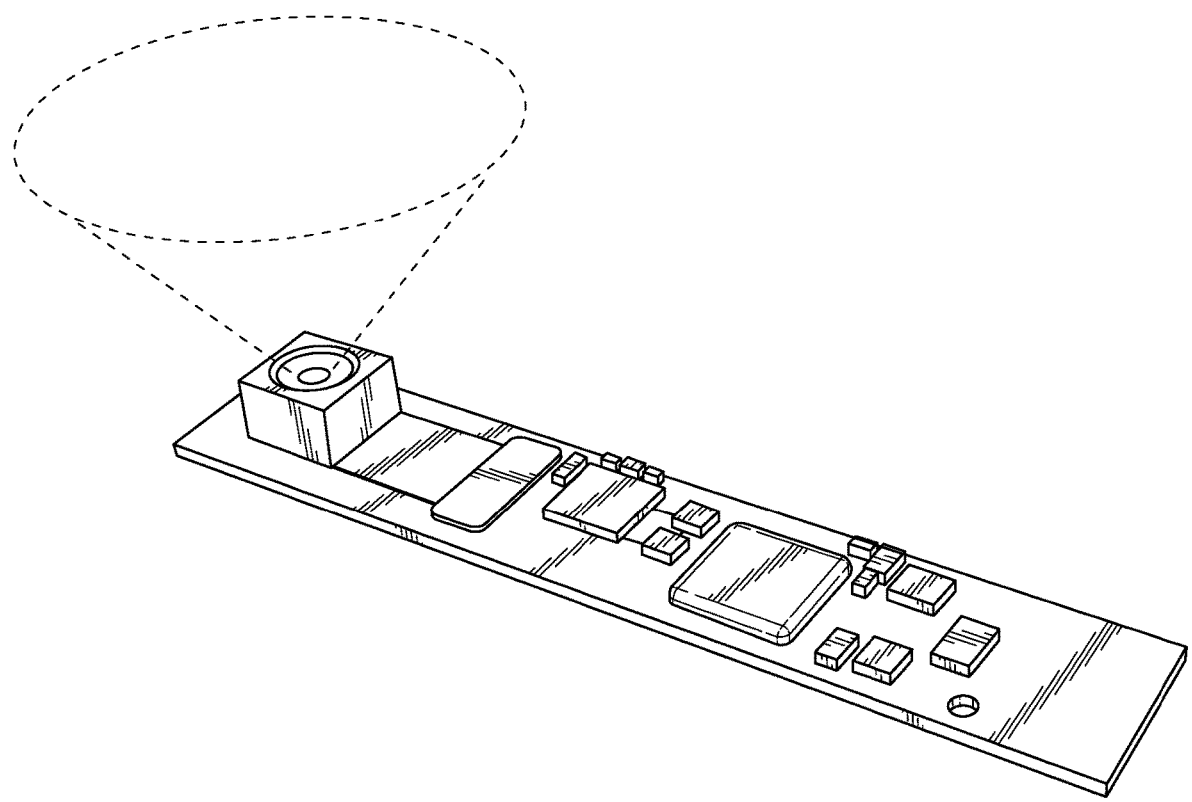
FIG. 7B is a perspective view of an embodiment of an imaging circuit board configured to mount within the radial extension and/or port body for example.

The port body 101 and the radial extension 105 can form a boot shape, e.g., as shown. The radial extension 105 can be a boot tip of the boot shape, for example. In certain embodiments, the radial extension 105 extends from the port body 101 a distance that is about equivalent to a widest part of the port body 101 or less. The imaging device cavity 107 can be positioned about halfway or more along a radial length of the radial extension 105. The instrument channel 101 and the imaging device cavity 107 can be configured such that an instrument channel centerline 129 and an imaging device field of view centerline 109a can intersect. For example, as shown in FIG. 6, the field of view centerline 109a is shown as substantially vertical, and the field of view is shown having a size of about 75 degrees (e.g., 74.4 degrees). The instrument channel centerline 129 is angled about 30 degrees and is shown intersecting the field of view centerline 109a at an about 80 mm arc. Any other suitable field of view size, angles, sizes, and/or distances are contemplated herein.

In certain embodiments, the device 100 can further include an instrument seal 131 disposed at distal opening 103a of the instrument channel 103. The device 100 can further include an imaging device 119 disposed within the imaging device cavity 107 and having a cable 115 extending through cable channel 113.

The device 100 can include a transparent cover 133 fixed to a distal side (e.g., continuous distal sides 101a, 105a) of the device 100 and covering the imaging device 119. The transparent cover 133 can include a hole 133a defined complimentary to the instrument channel 103 and/or configured to retain the instrument seal 133 in the instrument channel 103. The transparent cover 133 may also include an insufflation hole 133b complimentary to the insufflation port location (e.g., for inserting an insufflation or irrigation tube through channel 123).

In certain embodiments, the lip 125 can form a recessed surface 125a defined between the distal side 105a and the lip 125 of the device 100 which can provide a portion of a joint securing the transparent cover 133 to the radial extension 105, for example. The transparent cover 133 can be shaped to fit within and/or compliment the recessed surface 125a at a radial end 133c of the transparent cover 133 to create a tongue and groove joint. The transparent cover 133 can be attached to the distal surfaces 101a, 105a in any other suitable manner (e.g., additionally with adhesive). The transparent cover 133 can be sized to not block the one or more irrigation channel openings 127b when installed.

Any suitable size, shape, and materials for the transparent cover 133 are contemplated herein. For example, a glass surface is an example of material that can be used in the transparent cover 133. Other materials such as plastic may added or replace portions of the transparent cover 133 as desired or appropriate for optimal construction and performance. One or more coatings can be added to minimize fogging. These may include hydrophobic, hydrophilic, or antiglare surface coatings for example, and/or any other suitable coatings.

The device 100 can include an auxiliary module 121 configured to attach to a proximal side 101b (e.g., auxiliary module connector 101d) of the port body 101 and connect to the imaging device 119, for example. Any other suitable components (e.g., one or more lights, one or more light or imaging controllers, one or more circuit boards, one or more displays) are contemplated herein.

Figure 8:
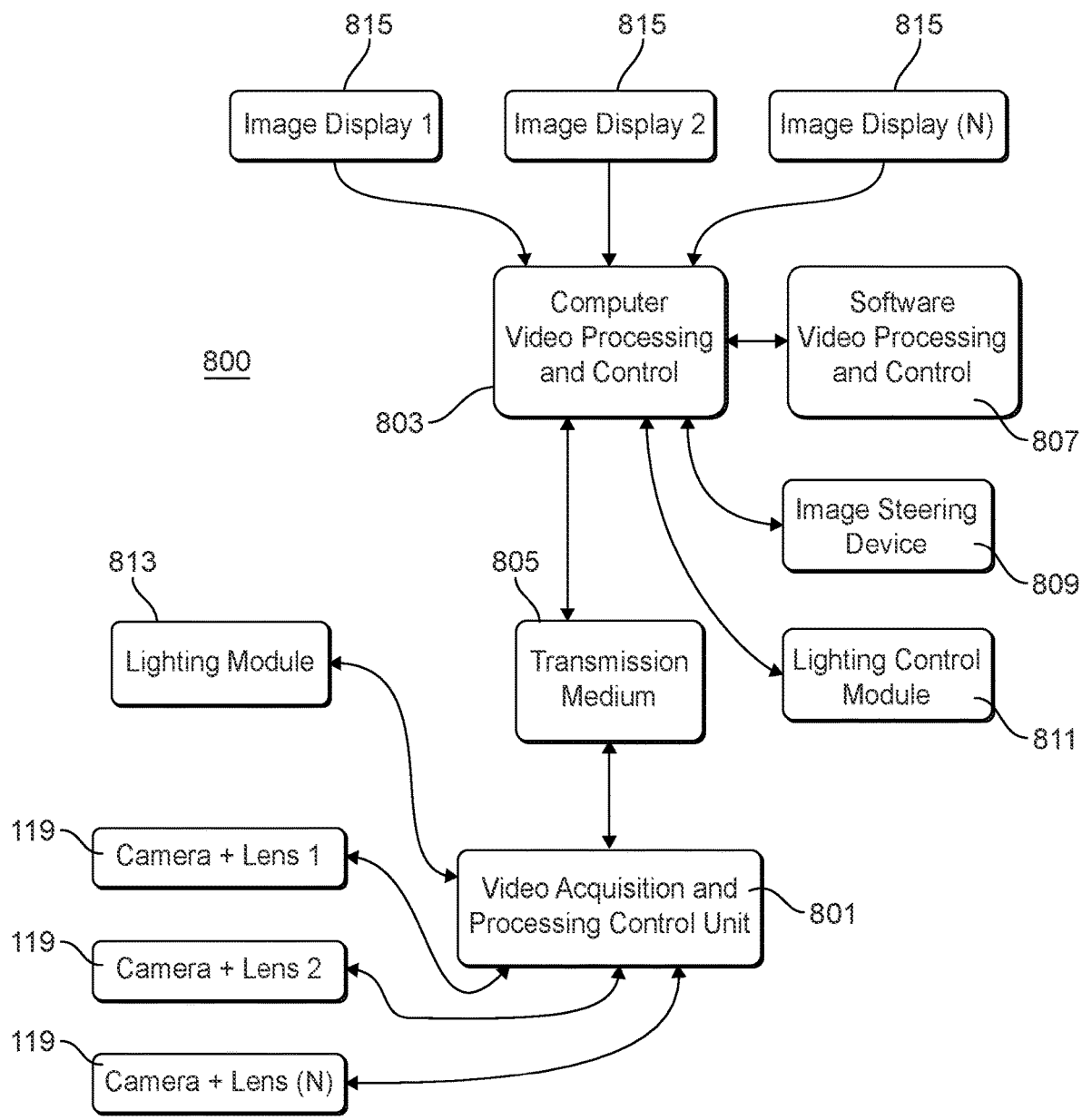
FIG. 8 is a schematic diagram of an embodiment of an imaging system in accordance with this disclosure.

For example, a system 800 as shown in FIG. 8 can include a lighting module, processing and control units, one or more displays, one or more lighting control modules, one or more software processing modules, one or more image steering devices, connected as shown. For example, the system 800 can include the video acquisition and processing control unit

Figure 9:
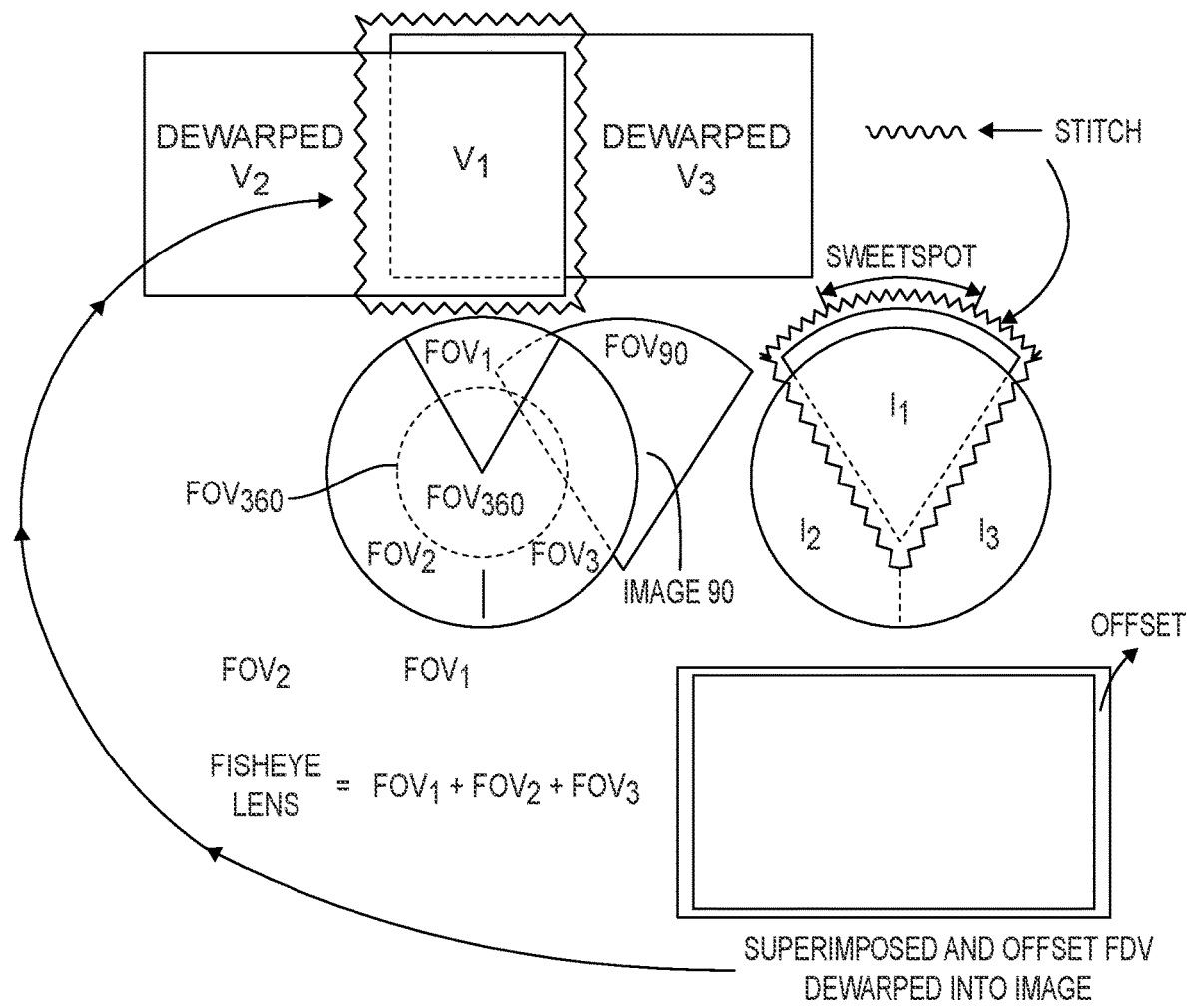
FIGS. 9 and 10 are schematic diagrams showing multi-camera use in accordance with at least one aspect of this disclosure.
Figure 10:
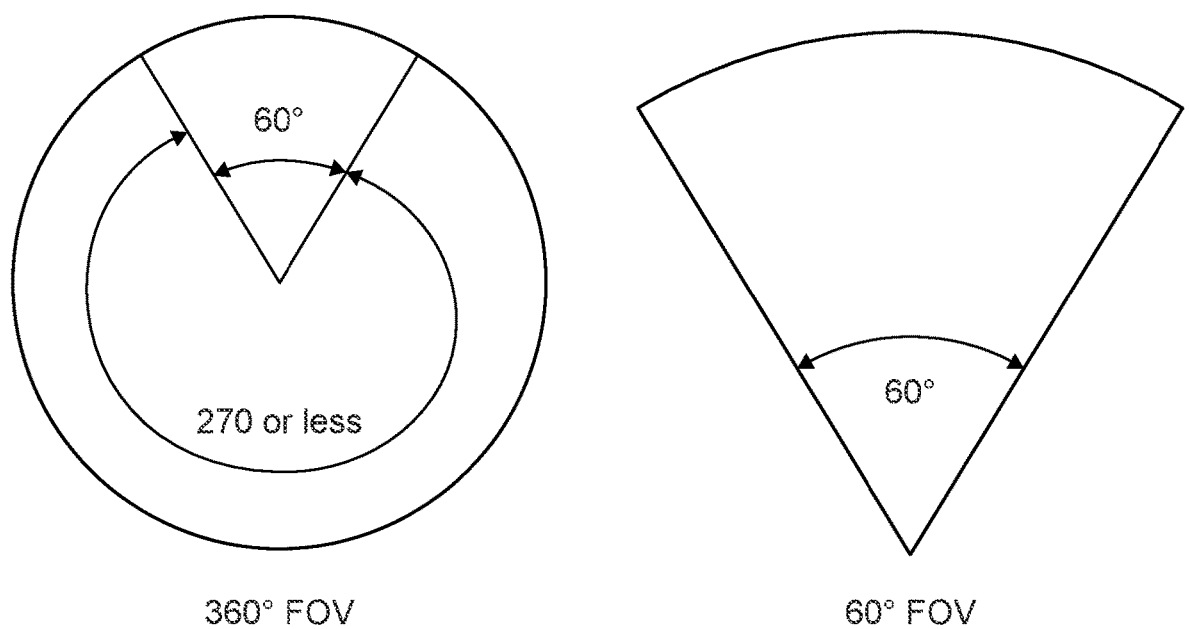

801 (e.g., circuit 117) connected to the imaging device 119. This unit 801 can be connected to a computer 803 for video processing and control via a transmission medium 805, e.g., a cable. The unit 801 can be connected to one or more imaging devices 119 (e.g., one or more cameras and/or lenses). The system 800 can include one or more software modules 807 (e.g., hosted on the computer 803) for processing video received from the unit 801. The system 800 can include one or more image steering modules 809 configured to digitally or physically steer a field of view of the one or more imagine devices 119. The system 800 can include a lighting control module 811 configured to control one or more lighting modules 813 (e.g., one or more LEDs in the device 100) to control a state (e.g., on, off, brightness, directionality, steering, etc.) thereof. One or more inputs and outputs can go through the computer 803, for example (e.g., steering, video processing, etc.). One or more image displays 815 can be connected to the computer 803 to display one or more images processed by the computer (e.g., for embodiments utilizing multiple imaging devices as shown in FIGS. 9 and 10). Any suitable image processing circuitry, connections, and logic are contemplated herein.

In accordance with at least one aspect of this disclosure, an imaging system for laparoscopic surgery can include an access device having an elongated body defining at least one access port and including a radial extension at a distal end thereof, a lighting device operatively associated with the radial extension of the access device, and at least one imaging device operatively associated with the radial extension of the access device.

The system can include a lighting control module for controlling the lighting device. The system can include a video control module for controlling the at least one imaging device. In certain embodiments, the system can include an image steering device operatively associated with the at least one imaging device. The system can include at least one image display device for displaying video acquired by the at least one imaging device.

As disclosed above, embodiments can include a circuit board in an auxiliary module structure. However, it is contemplated that the circuit board can be locating in any suitable auxiliary module (e.g., the auxiliary module as shown), the radial extension itself, and/or in the port body. A communication cable can extend from the auxiliary module (e.g., a USB 3 cable as shown in FIG. 1). Embodiments can include two branched irrigation channels, an insufflation channel, LED channels, and LED lights for example. The irrigation channel outlets can be positioned in the lip of the radial extension and face the imaging device camera to clean the transparent cover 133 where the imaging device is. Certain embodiment may include no moving parts and can include a field of view so large, that no parts need to move. The circuit board connected to the imaging device can be directly plugged in to a cable for suitable 4K data transfer at 30 fps, for example.

Referring to additionally to FIGS. 8-10, embodiments can include a new and useful surgical device is disclosed herein to obtain an image from a camera that is transmitted to a high resolution CMOS or CCD camera sensor mounted on the radial extension of and attached to the body of an access device as disclosed for example in commonly assigned U.S. Pat. No. 10,278,730, the disclosure of which is herein incorporated by reference in its entirety. The image can be processed and transmitted as an improved image to a monitor device selected by the surgeon, whether it be a typical monitor, flat or curved screen or an ocular virtual reality device positioned in proximity to the surgeon's eyes.

In certain embodiments, multiple light pipes can be incorporated into the construction of the access port body for transmission of light to the distal port surface. Illuminators in the form of a halo LED series can be positioned on an upper, proximal surface of the access port body to provide light to the light pipes embedded into the access port itself, for example. The distal light end of the light pipe can be shaped flat, semi-domed or domed. The halo circuit can be mounted on a printed circuit board (PCB). The external positioning of the LED lights can allow the heat produced by the LED to disperse to the mounting board and can be passively dispersed in the air. Any other suitable positioning for the lighting is contemplated herein.

Lighting of various formats can be projected from a PCB lighting halo ring to the base of the access port device emitting one or more types of light or energy including white light, color specific light, specific wave length of light, fluorescent light, or laser energy. Alternatively, light can also be provided by one or more lighting instruments inserted through the one or more instrument channels of the access device.

The lighting instrument can be constructed by mounting a PCB LED halo ring on a heat dispersing mounting board. Light pipes can be longitudinally embedded in polymer material to form a light pipe instrument shaft. The LED halo can be coupled to the light pipe shaft. The LED lighting can be carried by light pipes positioned within the one or more instruments passageways in the body of the device. The light pipe instrument can be inserted into the instrument conduit from the upper surface of the body of the access device to at least the lower surface of the body of the access device. An end connector to a power source can provide energy to the LED instrument.

One or more cameras can be mounted facing forward, to the side, or downward. Each camera may be used by itself or in conjunction with another camera on the access device or an accessory or separate access device. Images can be obtained by the one or more cameras mounted on the radial extension of the access device and communicated to the sensor board (CMOS). The image can be communicated to a high performance image signal processor (ISP). The data can be end coded on the ISP chip and then transmitted to a graphics processing unit (GPU) present on the computing device such as a laptop computer or desktop computer.

The ISP may have its own imaging processing capabilities to optimize and prepare the image data for transmission to the computer device therefore facilitating rapid processing of the data in the computer device. The computer device can process the image data to refine and optimize communication with the specific monitor for the application whether it be FPV, HD, HDR, stereoscopic, or 3D. Depending on the application, specific video software can be used to adjust for brightness, hue, color, contrast, de-warping, stitching, zoom, pan, tilt, rotation, alternating images, and superimposing images partially or in their entirety.

Embodiments remove dependency on a standard laparoscope allowing an imaging device to be built which collects and processes image to a computer-based processor which prepares the image for display on a monitor. Lighting can be separated from the image acquisition system. The view on the monitor can present all (global image) or a part (window image) of the image data depending on the specific utilization situation.

For the surgeon to use the device, the type of surgery can be determined and a standard appropriately sized incision can be made into a body space or cavity. The device can then be secured by stabilization contact sights on the port that are in contact with the body or organ wall. The device may also be stabilized with sutures as needed. The radial extension of the access device can then be pointed in the general direction of the target organ or field. The access imaging device allows for sealing of the operative space. For intraluminal spaces, other standard sealing mechanisms may be utilized as well.

The operative space can be insufflated with gas through a channel in the port device to provide a field of view. Fluid can be injected through a fluid channel in the port to cleanse the camera lens as needed. The access device can be independently positioned or further stabilized and/or adjusted with a retractor attached to the patient bed or to a robotic controlled device whichever is most suitable.

Referring to FIG. 8, the camera can be activated by connecting the access imaging module to a transmission line to the computer and activating power supplied to the camera and lighting devices. The type of light is selected to best provide the light required for the procedure. The brightness of light is adjusted and individual visual preferences are adjusted on the standard video software. A global image can then obtained from one or more cameras. The data can be transmitted to the standard video software to be processed to the desired type of image. This can then transmitted to the one or more monitors.

The global image can be a broad and detailed image obtained by the camera(s) and stored in the computer to be utilized. The global image can be the source of data used by the standard video software and the image steering device such as a joystick or a mouse. The image steering device can be connected to the computer and can be activated by its connection to the computer. The image window can be the area of image data to be transmitted to the one or more monitors after processing by the standard video software. The steering device can be moved or steered intuitively such that when it is turned to the right, the image projected as a window image has moved to the right on the global image. Likewise, the window image can be zoomed closer or farther on the global image data to render a close-up view or a stadium type view.

Once the camera has been placed in the zoom mode, the window image can be further directed to pan or tilt the window image and present adjacent image data to allow the surgeon or operator to look around at image data surrounding the primary image window yet still present on the global image and available for viewing by steering. This feature can aid in placing additional access ports and/or moving instruments under direct visualization. This can be an important safety feature for surgery.

Referring to FIGS. 10 and 11, two or more cameras can be used together on the radial extension of the access device as well as an additional camera on one or more percutaneous access devices. The two-camera mode can be selected and the geometrically aligned FOV from the two cameras can be processed in the video software to use a two-camera image aligned side by side, overlapped or superimposed.

The two-camera mode can also de-warp and stitch together the image data from the two or more cameras. The common overlap or "sweet-spot" can be used to provide even greater detail of a selected surgical area by combining the megapixels of each camera image. The stitched images can also be used to present a different image pattern to the monitor such as stereoscopic, 3D or holographic images.

Once the appropriate image is obtained for the surgical procedure, the planned surgery can be performed. After completion of the surgical procedure, the ports can be removed under direct vision using the steering device to appropriately image the site of various trocar sites. The access imaging device can be removed and the insertion site can be closed in a standard fashion.

Embodiments can include an imaging system for laparoscopic surgery, which can include an access device having an elongated body defining at least one instrument channel and including a radial extension at a distal end thereof, a lighting device operatively associated with the radial extension of the access device, and at least one imaging device operatively associated with the radial extension of the access device.

Among other features, the system can include a lighting control module for controlling the lighting device, a video control module for controlling the at least one imaging device, an image steering device operatively associated with the at least one imaging device, and at least one image display device for displaying video acquired by the at least one imaging device.

Certain embodiments provide an imaging device that is much smaller than current laparoscopes with the capability to acquire a detailed image and transmit the image data within a system that what would provide power, transmission, communication, steering, and software support for the performance of image guided surgery or interventions. In commonly assigned U.S. Pat. No. 10,278,730, incorporated herein in its entirety, there is described an improved access device having a radial extension that would advantageously provide a mechanical support structure to mount various types of useful imaging and lighting equipment of the type disclosed herein.

Laparoscopic surgery has relied on a device that is over 100 years old, the rigid laparoscope. The laparoscope is a large device requiring physical placement and steering generally through a tubular access device. Occasionally flexible endoscopy has been utilized to supplement rigid endoscopy. With the development of digital circuits and cameras, the size of the equipment and cameras has limited either the quality, transmission, or useful applications. Embodiments include a device which significantly expands the capability to acquire, process and transmit a larger amount of imaging data for intraoperative imaging.

Embodiments can include a radial extension that can be can be fixed or supported with its own mobility to bend, extend, and/or rotate. The access device as a whole can be controlled manually with a retractor and steered by manual or robotic mechanisms. The mounting surface of the radial extension can be flat-sloped or angled to optimize the camera positioning for the proposed procedure. The bottom surface to the body of the access device can also be used for mounting. In certain embodiments, a plurality of cameras may be aligned longitudinally, side by side or staggered geometric alignment to optimize imaging for a specific procedure.

Circuit boards and supporting equipment can be mounted it the radial extension and/or the body of the access device, as well as in a channel in the access device, for example. Any other suitable location is contemplated herein.

An image is obtained by a camera and communicated to the sensor board or device. The image can be communicated to a circuit board to communicate the pixel data to a computer processing device. The circuit board may also have its own imaging processing capabilities to optimize and prepare the image data to the computer device therefore facilitating rapid transmission for the date to the computer device. The computer device can process the image data to refine and optimize communication with the specific monitor for the application whether it be FPV, HD, HDR, stereoscopic, or 3D. Images can be obtained by the one or more cameras mounted on the radial extension of the access device and communicated to the sensor board (CMOS). The image can be communicated to a high performance image signal processor (ISP). The data can be end coded on the ISP chip and then transmitted to a graphics processing unit (GPU) present on the computing device such as a laptop computer or desktop computer. Any other suitable system components and/or logic are contemplated herein.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. An imaging system for laparoscopic surgery comprising:
   an access device having an elongated body defining at least one access port and including a radial extension at a distal end thereof;
   a lighting device disposed within the radial extension of the access device at a radially outward portion of the radial extension; and
   at least one imaging device disposed within the radial extension of the access device at a radially outward portion of the radial extension.

2. The system of claim 1, further comprising a lighting control module for controlling the lighting device.

3. The system of claim 1, further comprising a video control module for controlling the at least one imaging device.

4. The system of claim 1, further comprising an image steering device operatively associated with the at least one imaging device.

5. The system of claim 1, further comprising at least one image display device for displaying video acquired by the at least one imaging device.

6. The device of claim 1, further comprising an insufflation channel defined through the port body on an opposite side of port body from radial extension.

7. The device of claim 1, wherein the radial extension includes a lip extending distally from a radially outward portion of the radial extension, wherein the lip is outward of the imaging device cavity.

8. The device of claim 7, further comprising one or more irrigation channels defined through port body and the radial extension, such that one or more first irrigation openings are defined in the port body and one or more second irrigation openings are defined in the lip.

9. The device of claim 8, wherein the one or more irrigation channels at least partially travel around an instrument channel, travel outwardly, then curve back inwardly within the radial extension to the one or more irrigation outlets defined in the lip.

10. An imaging system for laparoscopic surgery comprising:
    an access device having an elongated body defining at least one access port and including a radial extension at a distal end thereof, wherein the radial extension includes a lip extending distally from a radially outward portion of the radial extension, wherein the lip is outward of the imaging device cavity, further comprising one or more irrigation channels defined through port body and the radial extension, such that one or more first irrigation openings are defined in the port body and one or more second irrigation openings are defined in the lip, wherein the one or more irrigation channels at least partially travel around the at least one access port, travel outwardly, then curve back inwardly within the radial extension to the one or more irrigation outlets defined in the lip;
    a lighting device operatively associated with the radial extension of the access device; and
    at least one imaging device operatively associated with the radial extension of the access device.

11. The imaging system of claim 10, wherein the at least one access porting is or includes an instrument channel.

12. An imaging system for laparoscopic surgery comprising:
    an access device having an elongated body defining at least one access port and including a radial extension at a distal end thereof, wherein the radial extension includes a lip extending distally from a radially outward portion of the radial extension, wherein the lip is outward of the imaging device cavity, further comprising one or more irrigation channels defined through port body and the radial extension, such that one or more first irrigation openings are defined in the port body and one or more second irrigation openings are defined in the lip, wherein the one or more irrigation channels at least partially travel around the at least one access port, travel outwardly, then curve back inwardly within the radial extension to the one or more irrigation outlets defined in the lip.

* * * * *